United States Patent
Ohishi et al.

(10) Patent No.: US 9,042,627 B2
(45) Date of Patent: May 26, 2015

(54) X-RAY DIAGNOSTIC APPARATUS, X-RAY DIAGNOSTIC METHOD AND STENT FOR X-RAY DIAGNOSIS

(75) Inventors: Satoru Ohishi, Otawara (JP); Yu-Bing Chang, Wheeling, IL (US)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 215 days.

(21) Appl. No.: 13/599,182

(22) Filed: Aug. 30, 2012

(65) Prior Publication Data

US 2013/0058556 A1 Mar. 7, 2013

(30) Foreign Application Priority Data

Sep. 2, 2011 (JP) .................... 2011-191315

(51) Int. Cl.
| | |
|---|---|
| G06T 7/00 | (2006.01) |
| A61B 6/12 | (2006.01) |
| A61F 2/06 | (2013.01) |
| G06K 9/00 | (2006.01) |
| A61B 6/03 | (2006.01) |
| A61F 2/82 | (2013.01) |

(52) U.S. Cl.
CPC ... *A61F 2/06* (2013.01); *G06K 9/00* (2013.01); *A61B 6/03* (2013.01); *A61B 6/12* (2013.01); *A61F 2/82* (2013.01); *A61F 2250/0098* (2013.01)

(58) Field of Classification Search
None
See application file for complete search history.

(56) References Cited

U.S. PATENT DOCUMENTS

| | | | |
|---|---|---|---|
| 5,835,561 A * | 11/1998 | Moorman et al. | 378/98 |
| 6,231,598 B1 | 5/2001 | Berry et al. | |
| 2001/0027339 A1 | 10/2001 | Boatman et al. | |
| 2007/0135707 A1 * | 6/2007 | Redel et al. | 600/424 |

(Continued)

FOREIGN PATENT DOCUMENTS

| | | |
|---|---|---|
| JP | 2001-517483 A | 10/2001 |
| JP | 2007-512070 A | 5/2007 |

(Continued)

OTHER PUBLICATIONS

Canero et al. "Optimal stent implantation: Three-dimensional Evaluation of the Mutual Position of Stent and Vessel Via Intracoronary Echocardiography." Computers in Cardiology, 1999, pp. 261-264.*

(Continued)

*Primary Examiner* — Jon Chang
(74) *Attorney, Agent, or Firm* — Oblon, McClelland, Maier & Neustadt, L.L.P.

(57) ABSTRACT

According to one embodiment, an X-ray diagnostic apparatus includes a data acquiring unit and a data processing unit. The data acquiring unit acquires X-ray projection data corresponding to plural directions from an object in which a stent having markers has been inserted by exposing X-rays to the object from the plural directions. The data processing unit obtains a spatial position corresponding to at least one marker out of the markers based on first three dimensional image data generated by first image reconstruction processing of the X-ray projection data to generate second three dimensional image data by second image reconstruction processing of the X-ray projection data with a correction using a shift amount obtained based on the X-ray projection data and projected data of the one marker on a projected plane of the X-ray projection data.

9 Claims, 6 Drawing Sheets

(56) References Cited

U.S. PATENT DOCUMENTS

| | | | |
|---|---|---|---|
| 2007/0263916 A1 | 11/2007 | Rasche et al. | |
| 2008/0137934 A1 | 6/2008 | Sakaguchi et al. | |
| 2010/0092063 A1 | 4/2010 | Sakaguchi | |
| 2010/0189218 A1 | 7/2010 | Sakaguchi et al. | |
| 2010/0228340 A1* | 9/2010 | Erbel et al. | 623/1.18 |
| 2010/0331950 A1* | 12/2010 | Strommer | 623/1.11 |

FOREIGN PATENT DOCUMENTS

| | | |
|---|---|---|
| JP | 2008-142543 A | 6/2008 |
| JP | 2010-115481 A | 5/2010 |
| JP | 2011-104353 | 6/2011 |

OTHER PUBLICATIONS

Perrenot et al. "Motion Correction for Coronary Stent Reconstruction From Rotational X-ray Projection Sequences." IEEE Transactions on Medical Imaging, vol. 26, No. 10, Oct. 2007, pp. 1412-1423.*

International Preliminary Report on Patentability and Written Opinion issued Mar. 13, 2014 in PCT/JP2012/071557 (English Translation only).

International Search Report and Written Opinion of the International Searching Authority issued Dec. 4, 2012, in PCT/JP2012/071557 (with English Translation of Category of Cited Documents).

Combined Chinese Office Action and Search Report issued Sep. 25, 2014 in Patent Application No. 201280001138.2 (with English Translation of Categories of Cited Documents).

* cited by examiner

X-RAY DIAGNOSTIC APPARATUS, X-RAY DIAGNOSTIC METHOD AND STENT FOR X-RAY DIAGNOSIS

CROSS REFERENCE TO RELATED APPLICATION

This application is based upon and claims the benefit of priority from Japanese Patent Application No. 2011-191315, filed Sep. 2, 2011; the entire contents of which are incorporated herein by reference.

FIELD

Embodiments described herein relate generally to an X-ray diagnostic apparatus, an X-ray diagnostic method and a stent for an X-ray diagnosis.

BACKGROUND

As one of imaging methods by an X-ray diagnostic apparatus, imaging using a stent is known. The stent is formed into a meshed tube using a strut having a structure like wires. Examples of typical stents used with an X-ray diagnostic apparatus include an intracranial stent.

The intracranial stent has a very thin strut. Therefore, it is difficult to observe the stent self by the X-ray diagnostic apparatus. Specifically, the strut of the intracranial stent has a cross-sectional diameter of approximately 60 μm. Accordingly, the conventional stent has markers so that a rough position of the stent can be known by imaging with an X-ray diagnostic apparatus. Specifically, four markers are arranged on a same circle forming one end of the stent at an equal interval. In addition, the other four markers are arranged at positions, on the other end side of the stent, derived by projecting positions of the four markers on the one end in the longitudinal direction.

Meanwhile, an X-ray diagnostic apparatus includes an X-ray detector having a high spatial resolution compared to an X-ray CT (computed tomography) apparatus. However, only markers can be observed mostly on a fluoroscopic image and an obtained image by an X-ray diagnostic apparatus. Note that, the strut of the stent can be observed by 3D (three dimensional) imaging.

By the way, the reproducibility not more than 100 μm of the rotation system and stasis of the strut are required for depicting the strut of the stent having a minute structure when a method of correcting a vibration using a vibration table acquired in the past, which is generally used for correction of a vibration or the like in 3D imaging by an X-ray diagnostic apparatus, is employed.

However, pressures placed on blood vessels near the stent changes due to the beat. Therefore, a motion due to changes in pressures of blood vessels sometimes occurs in the stent contacting the blood vessels. Further, it is sometimes difficult to keep a positioning error of a rotation system mounting an X-ray detector and X-ray tube under 100 μm in a conventional X-ray diagnostic apparatus.

Accordingly, an attempt to improve a stability of an X-ray diagnostic apparatus mechanically and an attempt to detect a minute change in position of a rotation system by a position sensor or the like so that the detected change in position can be corrected are made. However, these attempts bring a problem that a cost of X-ray diagnostic apparatus becomes high. Furthermore, it is sometimes difficult to observe a strut clearly because of a deviance of the strut due to a motion of an imaging part even though a displacement of a rotation system can be corrected entirely.

It is an object of the present invention to provide an X-ray diagnostic apparatus, an X-ray diagnostic method and a stent for an X-ray diagnosis which make it possible to depict a minute strut of stent by an easier way in imaging using the stent.

PRIOR TECHNICAL LITERATURE

Patent Literature

[Patent literature 1] JPA 2011-104353

DETAILED DESCRIPTION

In general, according to one embodiment, an X-ray diagnostic apparatus includes a data acquiring unit and a data processing unit. The data acquiring unit acquires X-ray projection data corresponding to plural directions from an object in which a stent having markers has been inserted by exposing X-rays to the object from the plural directions. The data processing unit obtains a spatial position corresponding to at least one marker out of the markers based on first three dimensional image data generated by first image reconstruction processing of the X-ray projection data to generate second three dimensional image data by second image reconstruction processing of the X-ray projection data with a correction using a shift amount obtained based on the X-ray projection data and projected data of the one marker on a projected plane of the X-ray projection data.

Further, according to one embodiment, an X-ray diagnostic method includes: acquiring X-ray projection data corresponding to plural directions from an object in which a stent having markers has been inserted by exposing X-rays to the object from the plural directions; and obtaining a spatial position corresponding to at least one marker out of the markers based on first three dimensional image data generated by first image reconstruction processing of the X-ray projection data to generate second three dimensional image data by second image reconstruction processing of the X-ray projection data with a correction using a shift amount obtained based on the X-ray projection data and projected data of the one marker on a projected plane of the X-ray projection data.

Further, according to one embodiment, a stent for an X-ray diagnosis includes a tubed strut and markers. Each of the markers is arranged on at least one end of said strut. At least one of the markers overlaps no other marker when the one is projected in a single direction different from an axial direction of said strut.

Further, according to one embodiment, a stent for an X-ray diagnosis includes a tubed strut and markers. The markers are arranged on both ends of said strut. Each of the markers overlaps no other marker when the markers are projected in an axial direction of said strut.

An X-ray diagnostic apparatus, an X-ray diagnostic method and a stent for an X-ray diagnosis according to embodiments of the present invention will be described with reference to the accompanying drawings.

First Embodiment

Figure 1:
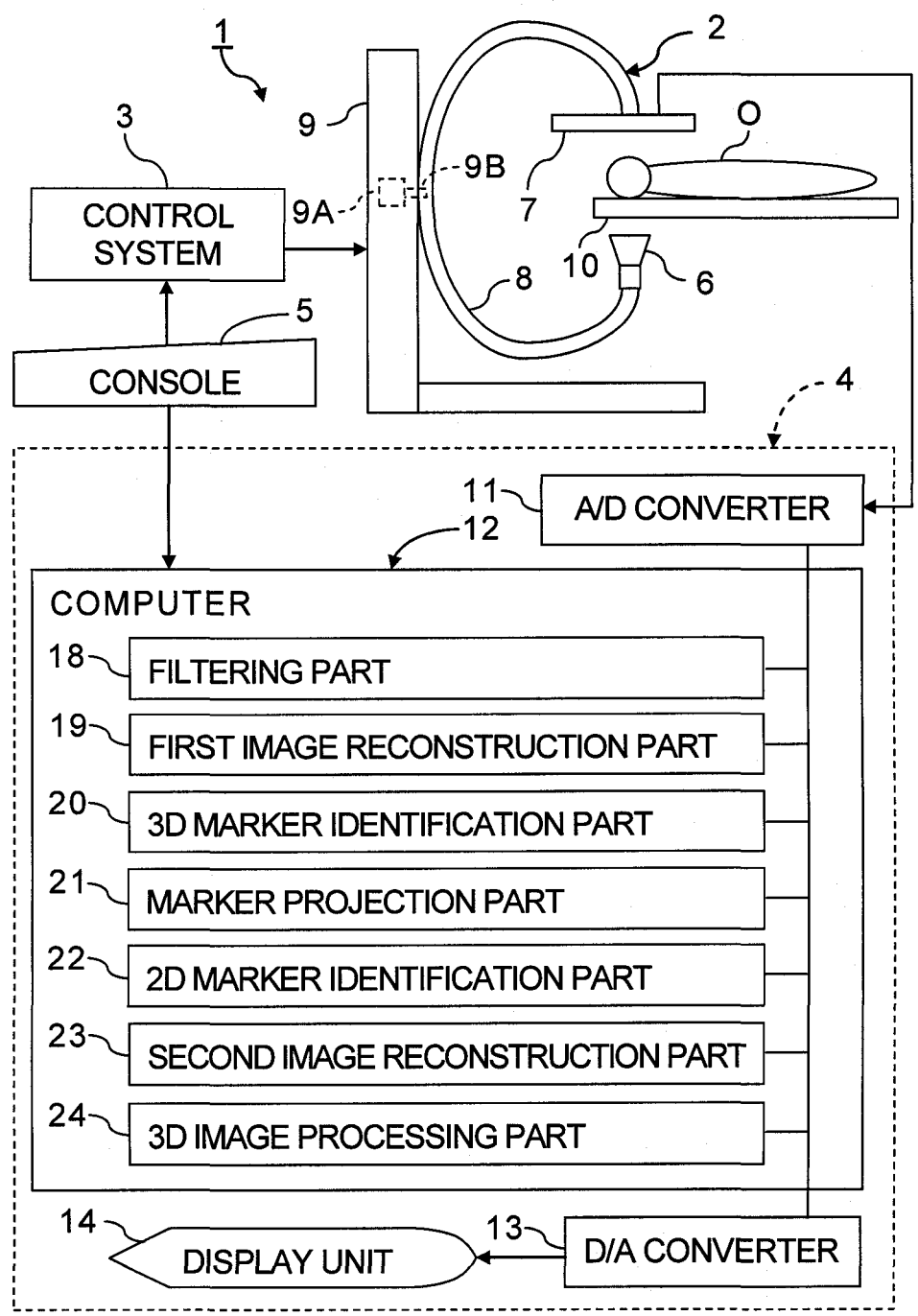
FIG. 1 is a configuration diagram of an X-ray diagnostic apparatus according to the first embodiment of the present invention.

FIG. 1 is a configuration diagram of an X-ray diagnostic apparatus according to the first embodiment of the present invention.

An X-ray diagnostic apparatus 1 includes an imaging system 2, a control system 3, a data processing system 4 and console 5. The imaging system 2 has an X-ray tube 6, an X-ray detector 7, a C-shaped arm 8, a base 9 and a bed 10. In addition, the data processing system 4 has an A/D (analog to digital) converter 11, a computer 12, a D/A (digital to analog) converter 13 and a display unit 14.

The X-ray tube 6 and the X-ray detector 7 are settled at both ends of the C-shaped arm 8 so as to be mutually opposed at both side of the interjacent bed 10. The C-shaped arm 8 is supported by the base 9. The base 9 has a motor 9A and a rotation mechanism 9B. The motor 9A and the rotation mechanism 9B drive so as to rotate the X-ray tube 6 and the X-ray detector 7 fastly into a desired position together with the C-shaped arm 8 like a propeller.

As the X-ray detector 7, a FPD (flat panel detector) or I.I.-TV (image intensifier TV) can be used. Furthermore, the output side of the X-ray detector 7 is connected with the A/D converter 11 of the data processing system 4.

The control system 3 drives and controls the imaging system 2 by outputting control signals to the respective elements consisting of the imaging system 2. The control system 3 is connected with the console 5 as an input device. Therefore, instruction of imaging conditions and the like to the control system 3 can be input from the console 5.

Then, the imaging system 2 is configured to expose X-rays toward an object O set on the bed 10 at mutually different angles sequentially from the rotatable X-ray tube 6 under control by the control system 3. In addition, the imaging system 2 is configured to acquire X-rays transmitting the object O from the plural directions sequentially as X-ray projection data by the X-ray detector 7.

Especially, the X-ray diagnostic apparatus 1 is configured to perform imaging of an imaging region including a stent inserted in an imaging part of the object O to depict a strut consisting of the stent. That is, the imaging system 2 can acquire X-ray projection data from a region including a stent inserted in an imaging part of an object O.

Figure 2:
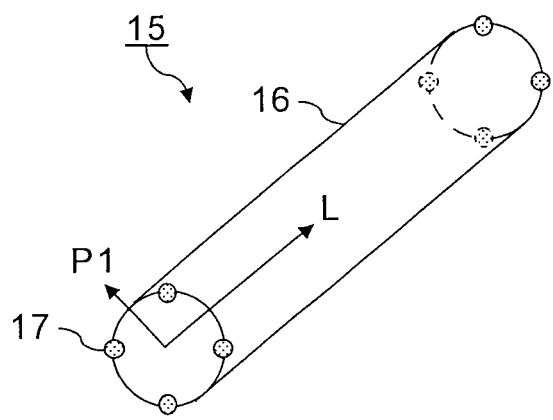
FIG. 2 is a perspective view showing a structure of a conventional stent which can be used together with the X-ray diagnostic apparatus shown in FIG. 1.

FIG. 2 is a perspective view showing a structure of a conventional stent which can be used together with the X-ray diagnostic apparatus 1 shown in FIG. 1.

As shown in FIG. 2, the conventional stent 15 is configured by arranging four markers 17 symmetrically and evenly at each end of a meshed and tubed strut 16. The stent 15 having such structure is inserted in a blood vessel including a neck of intracranial aneurism, i.e., a border between the aneurism and the blood vessel, or the like to be mainly used for a safe treatment in the blood vessel or the like.

The markers 17 is made by a matter showing a CT value higher than that of a reference matter around an imaging part. For example, a marker 17 for a stent used in an intracranial area is practically made by a material having a CT value higher than that of a bone or tooth.

Therefore, acquiring X-ray projection data from a region including a stent 15 allows generating image data depicting regions corresponding to the markers 17 as low signal values. In this case, the imaging system 2 functions as a data acquiring unit configured to acquire X-ray projection data corresponding to plural directions from an object O in which a stent 15 having markers 17 has been inserted by exposing X-rays to the object from the plural directions. So long as a similar function as the data acquiring unit is provided with the X-ray diagnostic apparatus 1, other elements may be used for constituting the data acquiring unit.

The conventional stent 15 shown in FIG. 2 has four markers 17 arranged on a same circle of each end part at an equal interval. Therefore, some markers 17 may overlap with each other according to a projection direction. For example, when X-ray projection data is acquired from a direction P1 vertical to the axial direction L, which is the longitudinal direction, of the strut 16, all markers 17 sometimes overlap mutually. In such a case, it may be difficult to distinguish the respective markers 17 mutually on image data reconstructed from X-ray projection data.

Accordingly, it is preferable to arrange the markers 17 at least at one end of the strut 16 so that at least one of the markers 17 does not overlap with any other marker 17 when the positions of the markers 17 are projected in a certain direction.

Figure 3:
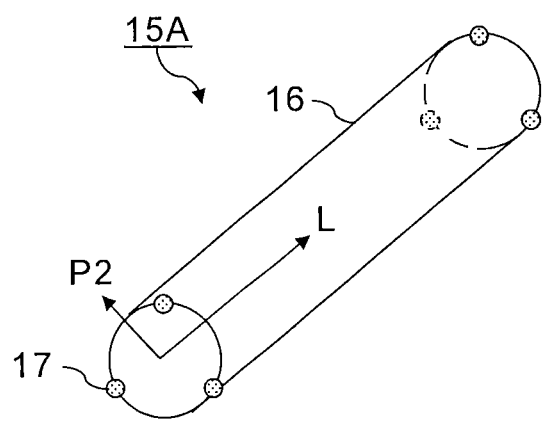
FIG. 3 is a perspective view showing an example of structure of a stent for an X-ray diagnosis, according to an embodiment of the present invention, which can be used together with the X-ray diagnostic apparatus shown in FIG. 1.

FIG. 3 is a perspective view showing an example of structure of a stent for an X-ray diagnosis, according to an embodiment of the present invention, which can be used together with the X-ray diagnostic apparatus 1 shown in FIG. 1.

The stent 15A shown in FIG. 3 is an example of configuration by arranging three markers 17 symmetrically and evenly at each end of the meshed and tubed strut 16. As shown in FIG. 3, determining the number of the markers 17 as an odd number makes it possible to arrange the markers 17 so that at least one of the markers 17 does not overlap any other marker 17 when the markers 17 are projected in a certain direction P2 at least different from the axial direction L of the strut 16.

Note that, if the number of the markers 17 set at one end of the strut 16 is set to be not less than five, adverse effect such that a structure and a manufacturing process of the stent become complex is assumed. Therefore, it is appropriate to arrange three markers 17 at one end of the strut 16 practically. Specifically, arranging three markers 17 on at least one end of the strut 16 makes it possible to prevent overlap of all markers 17 in case of projecting the markers 17 in a single direction P2 different from the axial direction L of the strut 16.

Furthermore, the markers 17 may be also arranged on each end of the strut 16 so that the markers 17 do not overlap mutually when positions of the markers 17 are projected in the axial direction L of the strut 16.

Figure 4:
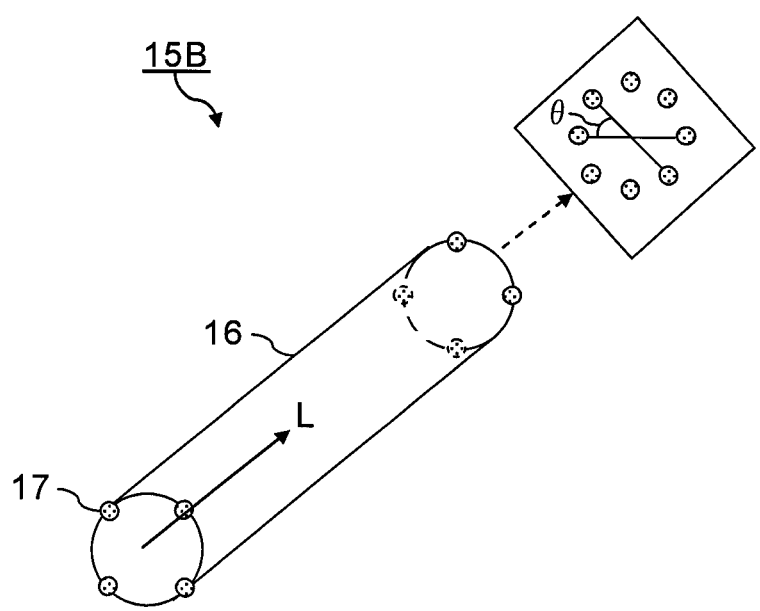
FIG. 4 is a perspective view showing another example of structure of a stent for an X-ray diagnosis, according to an embodiment of the present invention, which can be used together with the X-ray diagnostic apparatus shown in FIG. 1.

FIG. 4 is a perspective view showing another example of structure of a stent for an X-ray diagnosis, according to an embodiment of the present invention, which can be used together with the X-ray diagnostic apparatus 1 shown in FIG. 1.

The stent 15B in FIG. 4 shows an example of arranging four markers 17 evenly on each end of the meshed and tubed strut 16. If four markers 17 arranged on one end side are projected along the axial L of the strut 16, the projected four markers 17 lie on positions rotated from the other four markers 17 arranged on the other end side by a predetermined angle θ. Therefore, overlaps of the all markers 17 can be prevented when the positions of the all markers 17 are projected in parallel in a single direction which may be the axial direction L of the strut 16.

As described above, shifting arrangement of the four markers 17 on one end of the strut 16 of the conventional stent 15 from that of the other four markers 17 on the other end makes it possible to prevent mutual overlap of the markers 17 without changing the number of the markers 17.

Note that, it is preferable to arrange four markers 17 on each end of the strut 16 in view of making a manufacturing method easy and improving an effect for preventing mutual overlaps of the markers 17. In this case, one set of four markers 17 projected in the axial direction L of the strut 16 lie on positions rotated from those of the other set of four markers 17 by 45 degrees.

Of course, three markers 17 may be arranged on each end of the strut 16 so that positions of the markers 17, of one end side, projected in the axial direction L of the strut 16 do not overlap with those of the other markers 17 on the other end side. In this case, it is preferable to arrange three markers 17 on each end of the strut 16 so that one set of three markers 17 projected in the axial direction L of the strut 16 lie on positions rotated from those of the other set of three markers 17 by 60 degrees in view of making a manufacturing method easy and improving an effect for preventing mutual overlaps of the markers 17. As another example, a different number of markers 17 may be arranged on each end of the strut 16.

Next, a detailed function of the data processing system 4 will be described.

The output side of the A/D converter 11 in the data processing system 4 is connected with the input side of the computer 12. Meanwhile, the output side of the computer 12 is connected with the display unit 14 through the D/A converter 13. Furthermore, the computer 12 is connected with the console 5. Accordingly, instruction necessary for data processing can be input to the computer 12 by operation of the console 5.

Furthermore, the computer 12 functions as a filtering part 18, a first image reconstruction part 19, a 3D marker identification part 20, a marker projection part 21, a 2D marker identification part 22, a second image reconstruction part 23 and a 3D image processing part 24 by reading program. Note that, a circuit may be used for obtaining these functions to configure the data processing system 4.

The filtering part 18 has a function to apply necessary filter processing such as high frequency emphasizing filtering with X-ray projection data input to the computer 12 from the X-ray detector 7 through the A/D converter 11 and data generated based on the X-ray projection data.

The first image reconstruction part 19 has a function to perform image reconstruction processing based on pieces of X-ray projection data, corresponding to plural directions, input to the computer 12 from the X-ray detector 7 through the A/D converter 11 to reconstruct volume data as the first 3D image data from the pieces of the X-ray projection data corresponding to the plural directions.

The 3D marker identification part 20 has a function to identify a 3D position, in the 3D coordinate system, of at least one marker 17 out of the markers 17 arranged on the stent 15, 15A or 15B, based on the first 3D image data generated in the first image reconstruction part 19. Spatial positions of a single markers 17 or plural markers 17 can be obtained by threshold processing of the first 3D image data. Specifically, a CT value of the markers 17 is higher than that of a reference matter. Therefore, specifying points or regions, each showing a pixel value corresponding to a CT value larger than a threshold, from the first 3D image data by threshold processing makes it possible to identify spatial positions of markers 17 on the first 3D image data.

However, if any, matter other than a marker 17 and showing a CT value larger than that of a reference matter in an imaging region may lead to erroneously recognize a position of a marker 17 by threshold processing for identifying positions of markers 17. For example, a remaining metal as a treatment trace of a tooth may be erroneously recognized as a marker 17 by threshold processing for extracting parts showing CT values larger than that of a tooth.

Accordingly, the 3D marker identification part 20 can be provided with a function to specify candidates of markers 17 once by threshold processing of the first 3D image data and perform error processing to remove points and regions, other than markers 17, each erroneously recognized as a candidate of a marker 17. The error processing for removing candidates of markers 17 erroneously recognized based on the first 3D image data can be performed based on geometric information of the markers 17 arranged on the stent 15, 15A or 15B.

Specifically, a candidate of a marker 17 at a position which cannot be a position of a marker 17 can be removed as a erroneously recognized candidate based on known information including the known geometric information such as a size, a shape, a distance from another marker 17, a distance from the center of the strut 16 and a distance from the center of the first 3D image data of each marker 17 arranged on the stent 15, 15A or 15B. Herewith, a metal region remaining as a treatment trace of a tooth and the like can be removed from candidates of markers 17.

Furthermore, the 3D marker identification part 20 can also perform fitting of the extracted markers with an ideal marker shape based on a design specification. For example, a large motion of an imaging part sometimes distorts markers in the first 3D image data quite. A distortion of marker becomes a factor of error in post-processing. Accordingly, distortions of markers can be corrected by fitting of markers. The fitting of markers can be performed by identifying the (ΔX, ΔY, ΔZ) minimizing values $E_M(\Delta X, \Delta Y, \Delta Z)$ of expression (1).

$$E_M(\Delta X, \Delta Y, \Delta Z) = \sum_{\Delta X=-\Delta}^{\Delta} \sum_{\Delta Y=-\Delta}^{\Delta} \sum_{\Delta Z=-\Delta}^{\Delta} \left[ \frac{f(X, Y, Z) - f_0}{|f|} - \frac{g(X+\Delta X, Y+\Delta Y, Z+\Delta Z) - g_0}{|g|} \right]^2 \quad (1)$$

In expression (1), f(X, Y, Z) is a marker image extracted from the first 3D image data by threshold processing and g(X, Y, Z) is a function representing ideal shapes of markers. The g(X, Y, Z) becomes 1 in parts in which markers lie and 0 in the other parts. The $f_0$ and $g_0$ represent average values of the respective 3D images and the |f| and |g| represent energies of f(X, Y, Z)−$f_0$ and g(X+ΔX, Y+ΔY, Z+ΔZ)−$g_0$ respectively. That is, calculating a normalized cross correlation of f(X, Y, Z) and g(X, Y, Z) can identify the center coordinate of each marker 17. Note that, a rotation of each marker 17 is not considered here for simplifying description. However, it is desired to perform fitting in consideration of rotations of markers practically.

The marker projection part 21 has a function to obtain pieces of 2D projected data in case of projecting 3D image data of the markers 17, in the first 3D image data obtained by the 3D marker identification part 20, onto projected planes of the respective pieces of X-ray projection data. In other words, the marker projection part 21 has a function to obtain pieces of projected data of the markers on the respective projected planes. The calculating the pieces of the 2D projected data of the markers on the respective projected planes can be performed based on spatial coordinate information of projection systems respectively used for acquiring the respective X-ray projection data.

However, 2D projected positions of mutually different markers 17 may overlap with each other or become difficult to be distinguished in some projected directions of the X-ray projection data as described above. Especially, when the conventional stent 15 as shown in FIG. 2 is used, it often becomes difficult to distinguish 2D projected positions of mutually different markers 17.

Accordingly, each distance between 2D projected positions of adjacent markers 17 on the projected planes can be calculated in the marker projection part 21 to perform error processing for removing markers 17, corresponding to each calculated distance not more than a threshold, from calculating targets of the 2D projected positions. Alternatively, when a distance between 2D projected positions of adjacent markers 17 is not more than a threshold, a pair of the two adjacent markers 17 may be projected simultaneously. Furthermore, an arbitrary number of markers 17 may be projected simultaneously regardless of distances between 2D projected positions of the markers 17.

For example, in case of using the conventional stent 15 as shown in FIG. 2, the marker projection part 21 may project four markers 17 arranged on one end as one marker group. Alternatively, the marker projection part 21 may project only two adjacent markers 17, between which distance in 2D projected positions is not more than a threshold, as one marker group. The stent 15 has eight markers on the both ends. Therefore, in the latter case, 2D projected data of four to eight markers depending on a projected direction is to be calculated by the marker projection part 21.

The 2D marker identification part 22 has a function to identify 2D positions, on each projected plane, of the respective markers 17 arranged on the stent 15, 15A or 15B based on pieces of X-ray projection data corresponding to plural directions input from the X-ray detector 7 to the computer 12 and a function to obtain a shift amount between the identified 2D positions of the markers 17 and the 2D projected positions of the spatial positions of the markers 17 onto the projected plane of the X-ray projection data, as correction data.

For that purpose, the 2D marker identification part 22 is configured to obtain 2D projected data of each marker 17 or plural markers 17 from the marker projection part 21. When 2D projected data of plural markers 17 has been calculated, the plural markers 17 are identified simultaneously by the 2D marker identification part 22. Then, a shift amount between the identified 2D positions and the 2D projected positions is calculated as correction data. When plural pieces of correction data have been calculated, an average may be calculated. In this case, correction data influenced by less noise can be obtained. In addition, error processing for removing extremely abnormal correction data from calculation processing of an average by comparison of correction values may be performed in order to prevent reduction in calculation accuracy of the correction data.

2D positions of actual markers 17 on X-ray projection data appear as very small local minimal values of signals. Therefore, 2D positions of markers 17 can be identified by arbitrary signal processing for detecting very small local minimal values and positions corresponding to the local minimal values with a high accuracy. The displacement amount of markers 17 can be calculated by identifying the $(\Delta y, \Delta z)$ minimizing a value $E_p(\Delta y, \Delta z)$ of expression (2).

$$E_p(\Delta y, \Delta z) = \sum_{\Delta y=-\Delta'}^{\Delta'} \sum_{\Delta z=-\Delta'}^{\Delta'} \left[ \frac{p(y, z) - p_0}{|p|} - \frac{q(y+\Delta y, z+\Delta z) - q_0}{|q|} \right]^2 \quad (2)$$

In expression (2), p(y, z) is image data obtained by the logarithmic transformation of X-ray projection data and q(y, z) is marker image data projected by the marker projection part 21. The $p_0$ and $q_0$ represent average values of the respective pieces of the image data, and $|p|$ and $|q|$ represent energies of $p(y, z)-p_0$ and $q(y+\Delta y, z+\Delta z)-q_0$ respectively. That is, calculating a normalized cross correlation of p(y, z) and q(y, z) can identify the displacement of the markers 17.

The second image reconstruction part 23 has a function to generate the second 3D image data by the second image reconstruction processing of X-ray projection data with a correction using the correction data obtained by the 2D marker identification part 22.

Specifically, the displacement amount of the 2D projected positions of markers 17 from the actual 2D positions can be considered as an error in the reproducibility of the positions of the markers 17. Accordingly, correction processing for canceling the displacement amount of the markers 17 is performed to the X-ray projection data corresponding to each projected direction. Consequently, a minute displacement of an imaging part due to errors in a positioning accuracy of the imaging system 2 and motions of an object O can be corrected. Then, the second 3D image data having a higher spatial resolution can be generated by the second image reconstruction processing based on the X-ray projection data after the correction of the minute displacement.

As described above, a function to perform error processing may be provided with the marker projection part 21 or the 2D marker identification part 22. In addition, a function to obtain a position representing plural markers 17 may be provided with the marker projection part 21 and the 2D marker identification part 22. Then, positional correction processing with high accuracy can be performed based on position information of the markers 17 even if a part of the markers 17 overlap mutually. Especially, using the stent 15A or 15B shown in FIG. 3 or FIG. 4 makes it possible to perform appropriate correction processing with high accuracy based on position information of markers 17 which do not overlap on the projected plane even if a part of the markers 17 overlap mutually.

The 3D image processing part 24 has a function to generate 2D image data for displaying by 3D image processing based on one of or both the first 3D image data generated by the first image reconstruction part 19 and the second 3D image data generated by the second image reconstruction part 23, a function to display the generated 2D image data for displaying on the display unit 14 through the D/A converter 13.

Examples of the 3D image processing include various processing, such as MIP (maximum intensity projection) processing, MPR (multi-planar reconstruction) processing, VR (volume rendering) processing or SR (surface rendering) processing, for generating 2D image data from 3D image data. A kind of image processing and conditions of image processing can be set by inputting instruction from the console 5 to the 3D image processing part 24.

In the example described above, the computer 12 to which program is installed functions as a data processing unit configured to obtain a spatial position corresponding to at least one marker 17 out of the markers 17 based on first three dimensional image data generated by first image reconstruction processing of the X-ray projection data to generate second three dimensional image data by second image reconstruction processing of the X-ray projection data with a correction using a shift amount obtained based on the X-ray projection data and projected data of the one marker 17 on a projected plane of the X-ray projection data. However, the data processing unit may be configured by other elements so long as a similar function as a data processing unit is provided with the X-ray diagnostic apparatus 1.

Next, the operation and action of the X-ray diagnostic apparatus 1 will be described.

Figure 5:
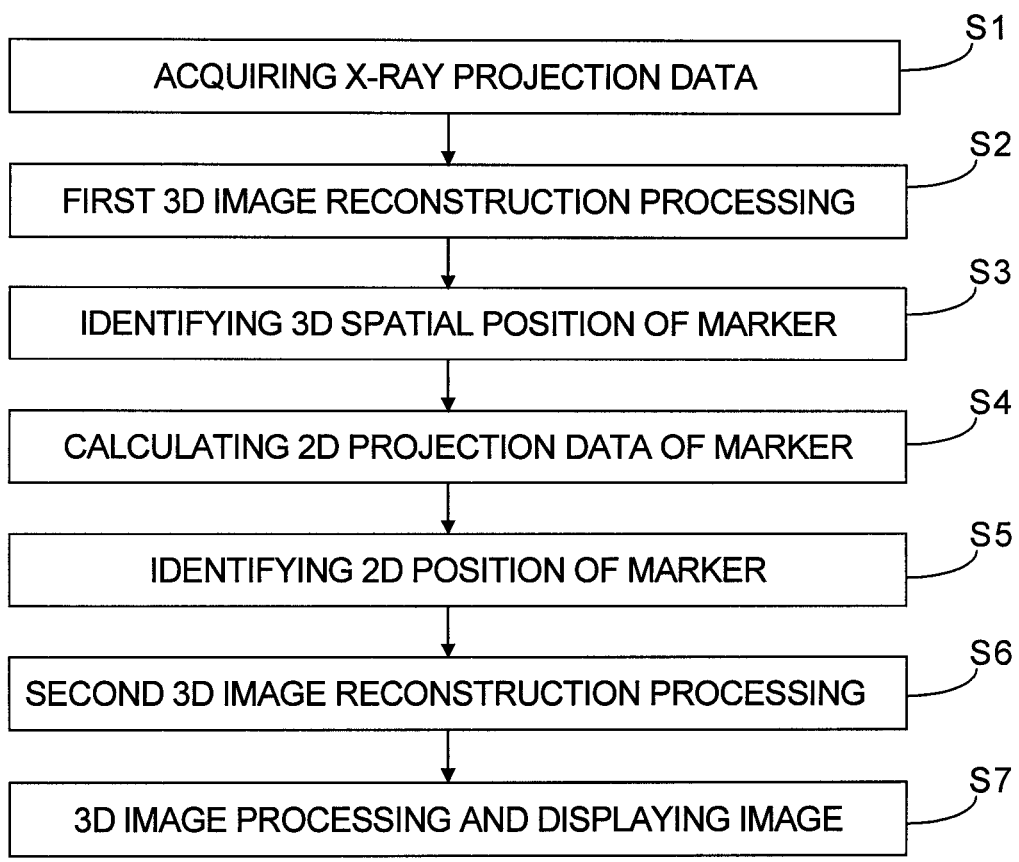
FIG. 5 is a flowchart showing a flow for imaging an object in which a stent has been inserted by the X-ray diagnostic apparatus shown in FIG. 1.

FIG. 5 is a flowchart showing a flow for imaging an object O in which a stent 15, 15A or 15B has been inserted by the X-ray diagnostic apparatus 1 shown in FIG. 1.

Firstly, in step S1, the imaging system 2 is driven under control by the control system 3. Then, the imaging system 2 exposes X-rays from plural directions to an object O, in which a stent 15, 15A or 15B having plural markers 17 has been inserted, to acquire pieces of X-ray projection data corresponding to the plural directions from the object O.

More specifically, the C-shaped arm 8 rotates to be a predetermined angle by driving the motor 9A and the rotation mechanism 9B settled on the base 9. Then, an X-ray is exposed from the X-ray tube 6 toward the object O set on the bed 10. Consequently, the transmitted X-ray from the object O is detected as X-ray projection data by the X-ray detector 7.

The exposure of an X-ray and detection of X-ray projection data are repeated with changing the projected angle by rotation of the C-shaped arm 8. For example, the projected angle is changed at an interval of 1 degree. Then, intensity distributions of transmitted X-rays for 200 degrees can be acquired as 200 patterns of X-ray projection data.

Acquiring X-ray projection data may be performed after injection of a contrast agent depending on a diagnosis purpose. When contrast enhanced imaging of the object O is performed by injecting a contrast agent, the contrast agent is injected into the object O by a contrast agent injector prior to acquire the X-ray projection data. Then, acquisition of the X-ray projection data is performed at about 50 degrees/second of a rotation velocity of the imaging system 2 after a predetermined period has been elapsed from a timing of injecting the contrast agent.

The pieces of the X-ray projection data for about 200 frames acquired by the X-ray detector 7 as described above are output to the data processing system 4. Then, the pieces of the X-ray projection data input to the data processing system 4 are converted into digital signals by the A/D converter 11 and subsequently output to the computer 12.

Next, in step S2, the pieces of the X-ray projection data converted into the digital signals are transmitted to the first image reconstruction part 19. The first image reconstruction part 19 reconstructs 3D volume image data as the first 3D image data from the pieces of the X-ray projection data by the first 3D image reconstruction processing of the pieces of the X-ray projection data.

As a method of image reconstruction processing, various methods are known. Here, an example case of image reconstruction processing under the filtered back projection method suggested by Feldkamp et al. will be described. Of course, a desired method of image reconstruction processing such as the successive approximation method can be used as well as the filtered back projection method.

Figure 6:
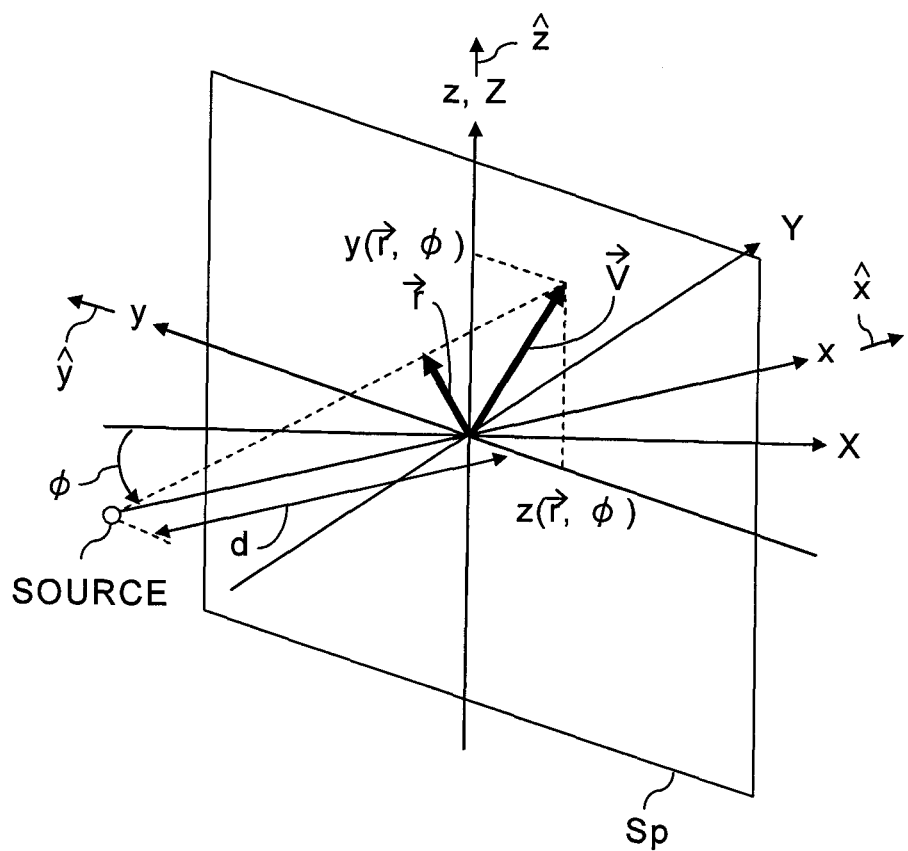
FIG. 6 is a diagram showing a coordinate system and a definition of parameters used for data processing in the data processing system shown in FIG. 1.

FIG. 6 is a diagram showing a coordinate system and a definition of parameters used for data processing in the data processing system 4 shown in FIG. 1.

As shown in FIG. 6, a 3D fixed coordinate system (X, Y, Z) and a 3D rotating coordinate system (x, y, z) rotated from the fixed coordinate system by an angle $\phi$ can be defined. In this case, a vector r is projected into the vector V having components (y, z) on the projected plane Sp by a cone beam of an X-ray exposed from the X-ray tube 6 as the X-ray source on the rotating x axis.

Meanwhile, a region for image reconstruction can be defined as a cylinder inscribing the X-ray bundle toward all directions from the bulb of the X-ray tube 6. Inside of the cylinder is separated by a distance d of the X-ray, at the center of the reconstructed region, projected into the width of one X-ray detection element included on the X-ray detector 7. Then, image data is obtained at the discrete points. Note that, the discrete interval may be defined for each apparatus instead of the distance d.

In case of image reconstruction processing by the filtered back projection method, 3D image data f generated by the image reconstruction processing is expressed by expression (3) using the coordinate system and the parameters shown in FIG. 6.

$$f(\vec{r}) = \frac{1}{4\pi^2} \int_0^{2\pi} W_2(\vec{r}, \phi) \tilde{P}_\phi \{y(\vec{r}, \phi), z(\vec{r}, \phi)\} d\phi \quad (3)$$

wherein $W_2$ in expression (3) is a weighting function represented by expression (4).

$$W_2(\vec{r}, \phi) \frac{d^2}{\{d + \vec{r}\hat{x}(\phi)\}^2} \quad (4)$$

Furthermore, (y, z) in expression (3) indicates the point on which the vector r is projected by the cone beam of the X-ray. The (y, z) is expressed as expression (5).

$$\left. \begin{array}{l} y(\vec{r}, \phi) = \dfrac{\vec{r}\hat{y}(\phi)d}{d + \vec{r}\hat{x}(\phi)} \\[6pt] z(\vec{r}, \phi) = \dfrac{\vec{r}\hat{z}(\phi)d}{d + \vec{r}\hat{x}(\phi)} \end{array} \right\} \quad (5)$$

wherein $\hat{x}(\phi)$, $\hat{y}(\phi)$, $\hat{z}(\phi)$ are unit vectors defining the directions of the x, y and z axes respectively.

Furthermore, $\tilde{P}_\phi(y, z)$ in expression (3) is expressed as expression (6).

$$\tilde{P}_\phi(y,z) = \{P_\phi(y,z)W_1(y,z)\} * g(y) \quad (6)$$

wherein * is the convolution operator, $P_\phi(y, z)$ is subtraction data obtained from the X-ray projection data, $W_1(y,z)$ is a weighting function and g(y) is a filter function. The filter function g(y) is a high frequency emphasizing filter for correcting blur due to the inverse projection operation. As a concrete example of the filter function g(y), a convolution filter such as Shepp-Logan filter or Ramachandran filter is typical.

Meanwhile, the weighting function $W_1(y, z)$ in expression (6) is expressed as expression (7).

$$W_1(y, z) = \frac{d}{\sqrt{d^2 + y^2 + z^2}} \quad (7)$$

As described above, the image reconstruction processing is expressed by expressions (3) to (7). Specifically, subtraction processing is firstly performed between each piece of the X-ray projection data for about 200 frames and image data for correcting unevenness in density. Next, the pieces of the subtraction data $P_\phi(y, z)$ for about 200 frames generated by the subtraction are weighted by the weighting function $W_1(y, z)$ as shown by expression (6). Subsequently, the convolution filter $g(y)$ is applied to the weighted pieces of the subtraction data.

Furthermore, 3D volume image data f after the image reconstruction can be obtained by the back projection operation, as shown by expression (3), of the data generated by the convolution operation.

Next, in step S3, the first 3D volume image data is sent to the 3D marker identification part 20. The 3D marker identification part 20 identifies 3D positions of the respective markers 17, arranged on the stent 15, 15A or 15B, in the 3D coordinate system, based on the first 3D volume image data.

For that purpose, parts each showing a CT value larger than that of a reference matter such as bone are extracted by threshold processing of the 3D volume image data at first. For example, regions of which pixel values are not less than a threshold set as 3000 are extracted.

The regions extracted by setting the threshold as 3000 consist of metal. Therefore, a metal for tooth treatment and the like may be extracted as candidates of the markers 17 as well as the markers 17 arranged on the stent 15, 15A or 15B.

Accordingly, the 3D marker identification part 20 performs error processing for removing erroneously recognized candidates of the markers 17 from the extracted candidates of the markers 17. The error processing can be performed by threshold processing with referring to geometric information of the markers 17, which is known information.

For example, the stent 15, 15A or 15B generally lies near the center of the field of view. Therefore, the candidates of the markers 17 within a certain distance from the center of the field of view can be selected as positions of the markers 17. Herewith, a metal for tooth treatment can be removed.

Alternatively, it is possible to perform error processing using a volume of a candidate of a marker 17. Specifically, s volume of a marker 17 is not more than 0.1 $mm^3$ while that of a metal for tooth treatment is at least 100 $mm^3$. Therefore, a metal for tooth treatment can be removed by selecting the candidates of the markers 17, of which volumes of regions are not more than a threshold, as positions of the markers 17.

Furthermore, as another example, error processing can also be performed with referring to the number of the markers 17. For example, when 10 candidates of the markers 17 are extracted though the number of the markers 17 is eight, two candidates of the markers 17 should be removed. For that reason, each relative distance between the candidates of the markers 17 can be calculated to remove the two candidates of the markers 17 corresponding to the two longer relative distances.

Next, the 3D marker identification part 20 calculates barycenters of the identified eight markers 17 and extracts minute regions, in which the markers lie, from the 3D volume image data as 3D marker image data.

Next, in step S4, the 3D barycenter positions of the identified markers 17 and the extracted 3D marker image data are sent to the marker projection part 21. The marker projection part 21 identifies 2D projected positions in case of projecting the 3D spatial positions of the markers 17 onto the projected planes of the frames f the respective X-ray projection data respectively. Further, frame of 2D projected image data are calculated in case of projecting the 3D marker image data onto the projected planes of the frames f the respective X-ray projection data respectively. The 2D projected positions and 2D projected image data can be calculated geometrically based on the projection systems corresponding to the respective projection directions for acquiring the frames of the X-ray projection data.

Next, the marker projection part 21 calculates each distance between the 2D projected positions of the markers 17. Then, each 2D projected position of a marker 17 corresponding to a distance between 2D projected positions not more than a threshold is removed. Consequently, 2D projected positions of markers 17 which may overlap mutually on each projected plane can be removed from data processing.

Alternatively, the marker projection part 21 calculates 2D projected image data representing plural markers 17, as needed. For example, 2D projected image data representing plural markers 17 of which each distance between 2D projected positions is not more than a threshold can be calculated. Furthermore, as another example, 2D projected image data representing plural markers 17 such as markers 17 arranged on one end of the stent 15, 15A or 15B can be also calculated regardless of distances between the 2D projected positions of the respective markers 17.

Next, in step S5, the calculated 2D projected image data of the markers 17 or the calculated 2D projected image data representing plural markers 17 is sent to the 2D marker identification part 22. Furthermore, the 2D marker identification part 22 obtains the frames of the X-ray projection data. Then, the 2D marker identification part 22 identifies 2D positions of the markers 17 on each projected plane or a 2D position representing plural markers 17 on each projected plane based on the frames of the X-ray projection data corresponding to the plural directions.

Specifically, the 2D marker identification part 22 can calculate a normalized cross correlation using the frames of the X-ray projection data and the 2D projected images of the markers 17 to calculate a displacement amount of the markers 17.

The correction data ($\Delta y$, $\Delta z$) can be obtained by expression (8) when a displacement amount of i-th marker 17 is denoted by ($\Delta y_i$, $\Delta z_i$). When the 2D projected positions and the 2D positions have been obtained as positions representing plural markers 17, the correction data ($\Delta y$, $\Delta z$) can be also obtained by a similar expression.

$$\left. \begin{array}{l} \Delta y = \dfrac{\sum_{i=1}^{N} (\Delta y_i)}{N} \\[2mm] \Delta z = \dfrac{\sum_{i=1}^{N} (\Delta z_i)}{N} \end{array} \right\} \quad (8)$$

wherein N is the number of positions of the markers 17 calculated and identified on each projected plane. Therefore, when eight markers 17 are arranged on the stent 15 or 15B and two markers 17 have been removed from processing for identifying 2D positions in the 2D marker identification part 22 by error processing in the marker projection part 21 for example, N=6. Alternatively, when eight markers 17 are arranged on the stent 15 or 15B and the marker projection part 21 has calculated two 2D projected positions each representing four markers 17, N=2.

Next, in step S6, the correction data (Δy, Δz) obtained as a shift amount in position of the markers 17 is transmitted to the second image reconstruction part 23. The second image reconstruction part 23 performs the second 3D image reconstruction processing of the X-ray projection data under an image reconstruction processing method similar to that performed in the first image reconstruction part 19.

However, a deviance in the position (y, z) of the projected point of the vector r is corrected using the correction data (Δy, Δz). Then, the position (y', z') of the projected point after the positional correction is used for the 3D image reconstruction processing. When the image reconstruction processing method is the filtered back projection method, the second 3D image reconstruction processing is performed using the position (y', z'), of the projected point after the positional correction, obtained by expression (9) instead of expression (5).

$$y'(\vec{r}, \phi) = \frac{\vec{r}\hat{y}(\phi)d}{d + \vec{r}\hat{x}(\phi)} + \Delta y \\ z'(\vec{r}, \phi) = \frac{\vec{r}\hat{z}(\phi)d}{d + \vec{r}\hat{x}(\phi)} + \Delta z$$ (9)

Then, the second 3D image data is generated from the X-ray projection data by the second 3D image reconstruction processing. The second 3D image data generated as described above becomes data subjected to the positional correction with high accuracy based on the shift amount between the 2D projected positions of the markers 17 obtained based on the 3D volume image data and the actual 2D positions of the markers 17. Therefore, even the minute strut 16 of the stent 15, 15A or 15B can be depicted.

Next, in step S7, various processing including processing for generating 2D data is performed for displaying the second 3D image data on the display unit 14. Subsequently, a 2D image for displaying is displayed on the display unit 14. That is, the 3D image processing part 24 performs 3D image processing for generating 2D image data for displaying from the second 3D image data.

Consequently, a user of the X-ray diagnostic apparatus 1 can observe an X-ray diagnostic image, depicting the strut 16 of the stent 15, 15A or 15B clearly, of an imaging part such as a head part of an object O.

That is, the X-ray diagnostic apparatus 1 described above is an apparatus configured to reconstruct an X-ray diagnostic image of which minute deviance in position is corrected by using positions of markers 17 arranged on the strut 16 of the stent 15, 15A or 15B as indexes. Specifically, spatial positions of markers 17 on volume image data generated by the first image reconstruction processing can be identified and subsequently the second image reconstruction processing can be performed with a displacement amount, between projected positions of the identified spatial positions on a projected plane and actual positions of the markers 17 searched near the projected positions on the X-ray projection data, as positional correction data.

Meanwhile, the respective stents 15A and 15B shown in FIG. 3 and FIG. 4 have plural markers 17 so that all of the markers 17 do not overlap on an arbitrary projected plane.

Therefore, the X-ray diagnostic apparatus 1 can depict a strut 16 of a stent 15, 15A or 15B more clearly than the conventional apparatus even though the stent moved minutely due to the beat or the rotational reproducibility of the imaging system 2 cannot be kept in a value not more than 50 μm constantly. Consequently, a user becomes possible to know relationship between a strut 16 and a blood vessel.

Furthermore, using a stent 15A or 15B as shown in FIG. 3 or FIG. 4 makes it possible to correct a minute positional deviance steadily using positions of the markers 17 as indexes regardless of projected angles.

Second Embodiment

Figure 7:
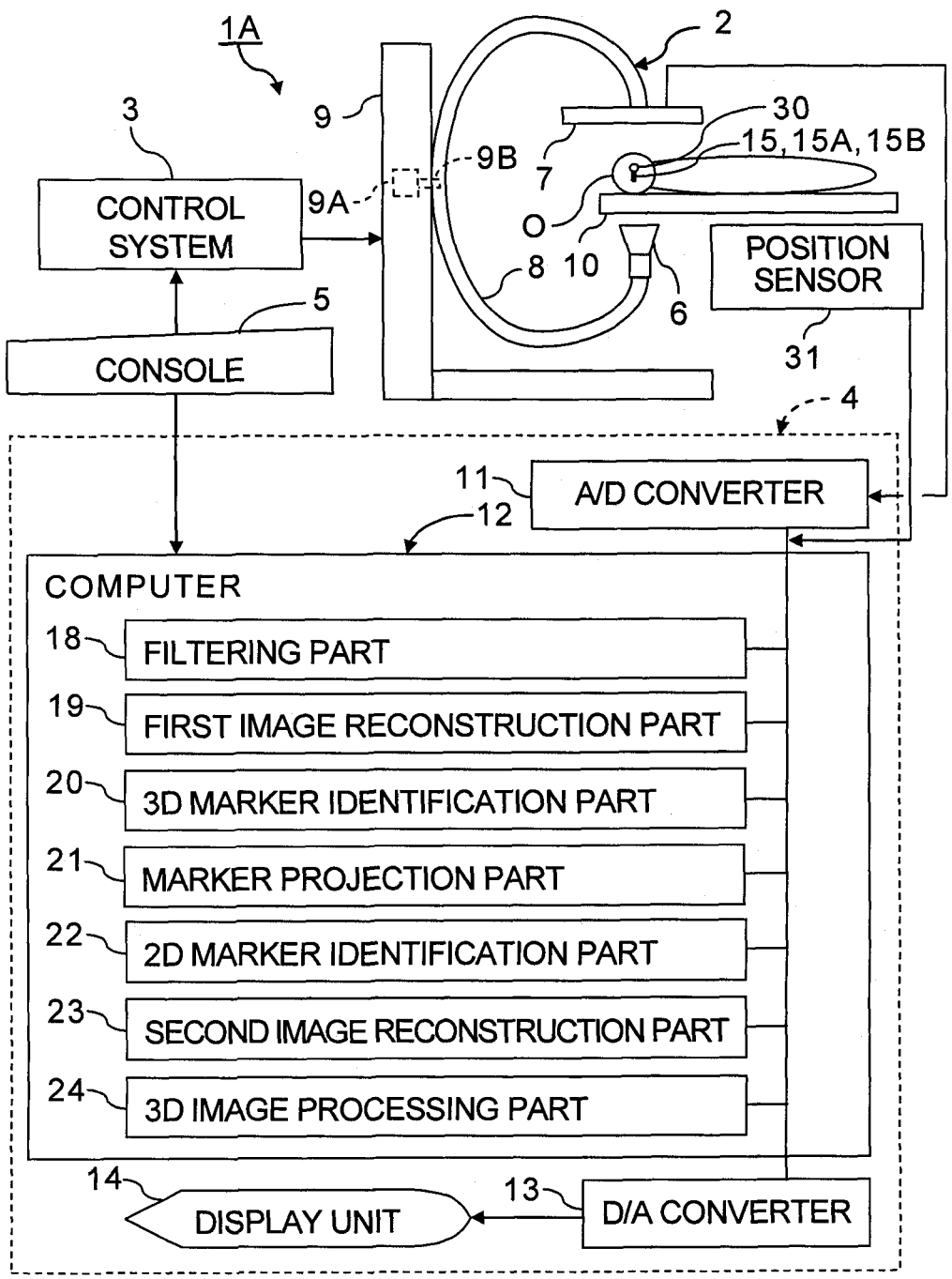
FIG. 7 is a configuration diagram of an X-ray diagnostic apparatus according to the second embodiment of the present invention.

FIG. 7 is a configuration diagram of an X-ray diagnostic apparatus according to the second embodiment of the present invention.

An X-ray diagnostic apparatus 1A shown in FIG. 7 is different from the X-ray diagnostic apparatus 1 shown in FIG. 1 in a point that a position sensor 31 for transmitters 30 attached to markers 17 of a stent 15, 15A or 15B is provided and detailed function of the 3D marker identification part 20. The other constructions and operations of the X-ray diagnostic apparatus 1A are not different from those of the X-ray diagnostic apparatus 1 shown in FIG. 1 substantially. Therefore, the same numbers are attached to the same elements and explanation thereof is omitted.

Specifically, an object O in which a stent 15, 15A or 15B having markers 17 has been inserted is set on the bed 10 of the X-ray diagnostic apparatus 1A. However, the transmitters 30 are attached to the markers 17 of the stent 15, 15A or 15B respectively.

Meanwhile, the imaging system 2 includes the position sensor 31. The position sensor 31 has a function to receive wireless signals transmitted from the transmitters 30 attached to the markers 17 of the stent 15, 15A or 15B respectively and a function to detect spatial positions of the transmitters 30 or the markers 17 based on the received wireless signals. For an algorithm for detecting the positions, known one can be used.

Therefore, the position sensor 31 is arranged at a desired position at which signals transmitted from the transmitters 30 of the stent 15, 15A or 15B can be received with a sufficient accuracy. The output side of the position sensor 31 is connected with the computer 12 of the data processing system 4. Then, the position sensor 31 is configured to output a detection result of spatial positions of the transmitters 30 or the markers 17 to the computer 12 as digital data.

Meanwhile, the 3D marker identification part 20 of the computer 12 has a function to obtain the detection result of the spatial positions of the transmitters 30 or the markers 17 output from the position sensor 31 and a function to obtain spatial positions of the markers 17 in the 3D coordinate system based on the obtained detection result of the spatial positions of the transmitters 30 or the markers 17.

Then, the marker projection part 21 is configured to obtain 2D projected positions in case of projecting the 3D spatial positions of the markers 17, obtained by the 3D marker identification part 20, onto the respective projected planes of the frames of the X-ray projection data.

In the X-ray diagnostic apparatus 1A having such a structure, spatial positions of the transmitters 30 or the markers 17 are detected by the position sensor 31, based on signals transmitted from the transmitters 30 of the stent 15, 15A or 15B. Then, the 3D marker identification part 20 identifies 3D spatial positions of the markers 17 based on the spatial positions of the transmitters 30 or the markers 17 detected by the position sensor 31.

That is, the X-ray diagnostic apparatus 1A is an apparatus configured to identify 3D spatial positions of the markers 17 based on spatial positions of the transmitters 30 or the markers 17 detected by the position sensor 31 with attaching the transmitters 30 to the markers 17, instead of identifying the spatial positions of the markers 17 from 3D volume image data generated by the first image reconstruction processing like the X-ray diagnostic apparatus 1 shown in FIG. 1.

Therefore, the X-ray diagnostic apparatus 1A shown in FIG. 7 can generate X-ray diagnostic image data of which positions are corrected with high accuracy using positions of the markers 17 as indexes without complex data processing such as twice image reconstruction processing like the X-ray diagnostic apparatus 1 shown in FIG. 1. Consequently, an X-ray diagnostic image depicting a strut 16 of a stent 15, 15A or 15B more clearly than a conventional image can be obtained similarly to the X-ray diagnostic apparatus 1 shown in FIG. 1.

Other Embodiments

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, example cases of imaging an object O, in which a stent 15, 15A or 15B has been inserted, with the X-ray diagnostic apparatus 1 or 1A are described in the above-mentioned embodiments. However, it is also possible to depict a stent 15, 15A or 15B in imaging with an X-ray CT apparatus by similar image reconstruction processing as long as the X-ray CT apparatus includes an X-ray detector having a sufficient spatial resolution. That is, positional correction processing can be performed with high accuracy using markers 17 as indexes by an algorithm according to an image reconstruction method. Then, twice image reconstruction processing makes it possible to generate X-ray CT image data having a spatial resolution necessary for depiction of a stent 15, 15A or 15B.

What is claimed is:

1. An X-ray diagnostic apparatus, comprising:
a data acquiring unit, including an X-ray tube and an X-ray detector, configured to acquire X-ray projection data from an object, in which a stent having markers has been inserted, using the X-ray detector by exposing X-rays to the object from plural directions by the X-ray tube, the X-ray projection data corresponding to the plural directions; and
a data processing circuit configured to obtain a spatial position corresponding to at least one marker out of the markers based on first three dimensional image data generated by first image reconstruction processing of the X-ray projection data in order to generate second three dimensional image data by second image reconstruction processing of the X-ray projection data, the second image reconstruction processing being performed with a correction using a shift amount obtained based on the X-ray projection data and projected data of the at least one marker on a projected plane of the X-ray projection data.

2. An X-ray diagnostic apparatus of claim 1,
wherein said data processing circuit is configured to perform the second image reconstruction processing with the correction using a shift amount obtained based on the X-ray projection data and projected data of arbitrary plural markers on the projected plane.

3. An X-ray diagnostic apparatus of claim 2,
wherein said data processing circuit is configured to use markers of which each distance from a marker adjacent in a projected position on the projected plane is not more than a threshold as the arbitrary plural markers.

4. An X-ray diagnostic apparatus of claim 1,
wherein said data processing circuit is configured to perform the second image reconstruction processing with the correction using only a shift amount corresponding to the at least one marker out of the markers, the at least one marker being away from a marker adjacent in a projected position on the projected plane by a distance longer than a threshold.

5. An X-ray diagnostic apparatus of claim 1,
wherein said data processing circuit is configured to perform error processing to detect an erroneous marker and to remove the detected erroneous marker detected based on the first three dimensional image data, the error processing being based on geometric information of the markers.

6. An X-ray diagnostic apparatus of claim 5,
wherein said data processing circuit is configured to use at least one of a size, a shape, a distance from another marker, a distance from a center of a strut of the stent and a distance from a center of the first three dimensional image data of each marker as the geometric information of the markers.

7. An X-ray diagnostic apparatus of claim 1,
wherein said data processing circuit is configured to obtain the spatial position of the at least one marker by threshold processing of the first three dimensional image data.

8. An X-ray diagnostic apparatus of claim 1, further comprising:
a position sensor configured to receive a wireless signal transmitted from a transmitter attached to the markers to detect a position of the transmitter or the markers,
wherein said data processing circuit is configured to obtain the spatial position of the at least one marker based on the position of the transmitter or the markers detected by said position sensor.

9. An X-ray diagnostic method, comprising:
acquiring X-ray projection data corresponding to plural directions from an object in which a stent having markers has been inserted by exposing X-rays to the object from the plural directions; and
obtaining a spatial position corresponding to at least one marker out of the markers based on first three dimensional image data generated by first image reconstruction processing of the X-ray projection data in order to generate second three dimensional image data by second image reconstruction processing of the X-ray projection data, the second image reconstruction processing being performed with a correction using a shift amount obtained based on the X-ray projection data and projected data of the at least one marker on a projected plane of the X-ray projection data.

* * * * *